United States Patent [19]

Edward, Jr.

[11] 4,283,939
[45] Aug. 18, 1981

[54] DIAL GAUGE MOUNTING APPARATUS

[75] Inventor: Robert M. Edward, Jr., The Woodlands, Tex.

[73] Assignee: JB Development Corporation, The Woodlands, Tex.

[21] Appl. No.: 108,581

[22] Filed: Dec. 31, 1979

[51] Int. Cl.³ .............................................. G01N 3/42
[52] U.S. Cl. ...................................... 73/81; 33/172 R
[58] Field of Search ......................... 73/81, 83, 85, 78; 33/172 R

[56] References Cited

U.S. PATENT DOCUMENTS

| | | | |
|---|---|---|---|
| 1,037,596 | 9/1912 | Coppage | 73/81 |
| 1,768,639 | 7/1930 | Shore et al. | 73/81 |
| 2,360,760 | 10/1944 | Clark | 73/81 |
| 2,667,066 | 1/1954 | Ernst | 73/81 |
| 3,084,538 | 4/1963 | Small et al. | 73/83 |
| 3,182,491 | 5/1965 | Tschirf et al. | 73/81 |
| 3,881,256 | 5/1975 | Jewell et al. | 33/172 R |
| 3,956,925 | 5/1976 | Smith | 73/81 |

Primary Examiner—Daniel M. Yasich
Attorney, Agent, or Firm—Bill B. Berryhill

[57] ABSTRACT

Mounting apparatus for attaching a dial gauge to the housing of a hardness tester in which is carried a load cell. The dial gauge may have a housing in which is carried an operating mechanism and a dial indicator and from the base of which extends a plunger for engagement with the plunger rod of the load cell and responsive to movement thereof for actuating the operating mechanism and the dial indicator. The mounting may comprise: a cap member attachable to one end of the tester housing having a central aperture therethrough and a support member attached to the cap member to which is attached the dial gauge so that the dial gauge plunger is centrally and freely disposed in the cap member aperture. The cap member is attachable to the tester housing so that the dial gauge plunger engages the plunger rod centered in the load cell in a predetermined relationship but is removable so that the cap member, support member and dial gauge may be removed from the tester housing without relative movement therebetween.

2 Claims, 4 Drawing Figures

DIAL GAUGE MOUNTING APPARATUS

BACKGROUND OF THE INVENTION

1. Field of the Invention

The present invention pertains to mounting apparatus for hardness testers. Specifically, it pertains to apparatus for mounting dial gauges on load cell type hardness testers.

2. Brief Description of the Prior Art

Load cell type hardness testers conventionally comprise a housing in which is carried a load cell. The load cell is engageable at one end by an operating cam and a penetrator. The penetrator engages a plunger rod. The operating cam is normally provided with a handle, rotation of which allows a predetermined force to be applied to the penetrator to indent the material being tested. The load cell and the plunger rod respond in a predetermined fashion to the indentation of the penetrator in the material being tested. A dial gauge is attached to the tester for engagement with the opposite end of the plunger rod for measuring the response of the load cell to the hardness of the material being tested.

The mounting of the dial gauge on the tester is extremely critical. It must be mounted so that the dial indicator thereof is in a fixed relationship with the tester housing at all times. Such dial gauges are normally provided with a stem member at the base thereof and a reciprocating plunger member extending from the stem. In the past, the dial gauge has been attached to the tester with mounting apparatus which grips the stem member holding it in place. Such means of mounting may create problems by damaging the stem. In fact, the stem may be so damaged as to impair the reciprocation of the plunger member by which the mechanism operating the dial indicator is actuated.

Since the dial gauge must be occasionally removed for changing of load cells with different loads, recalibration, repair, or replacement, the mounting apparatus should be easily removed and reattachable so that the dial gauge is returned to the same relative position prior to removal. The attachment apparatus of the prior art is not easily removable and, when it is removed, it is almost impossible to reattach it in such a way that the dial gauge is in the same relative position with the tester as prior to removal therefrom.

SUMMARY OF THE INVENTION

With the mounting apparatus of the present invention, the housing of the dial gauge is attached to a support member which is in turn attached to a cap member, having a central aperture in which the dial gauge plunger is centrally and freely disposed without gripping of the dial gauge stem. The cap member is removably attached to the tester housing so that the dial gauge plunger engages the load cell in a predetermined relationship. The cap member, support member and dial gauge are removable from the tester, together as a unit, so that there is no relative movement therebetween. The cap member is reattachable to the tester so that the support member and dial gauge are in the same relative position as prior to removal.

Thus, the mounting apparatus of the present invention provides a means by which a dial gauge may be attached to a tester without gripping the stem thereof and the potential damage associated with such mounting. Furthermore, the mounting is more easily attached and removed than with prior art apparatus. Still further, reattachment in the same relative position is much more easily accomplished with the apparatus of the present invention. Other objects and advantages of the present invention will be apparent from reading the specification which follows in conjunction with the accompanying drawings.

DESCRIPTION OF PRIOR ART

Figure 1:
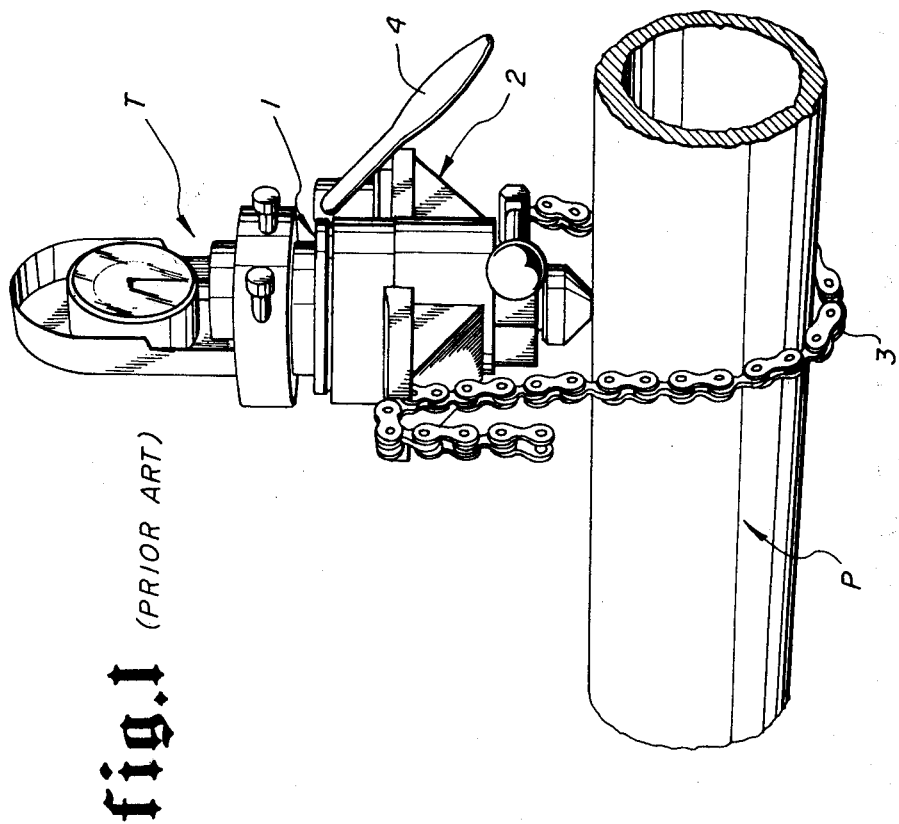
FIG. 1 is a pictorial illustration of a hardness tester mounted on a piece of pipe, by a chain assembly, for testing thereof.

Referring first to FIG. 1, there is shown a hardness tester T attached to a piece of pipe P for testing the hardness thereof. The tester T includes a head unit 1 which is carried in an attachment assembly 2 by which the tester T is attached to the pipe P. The attachment assembly shown is one of the chain type having a chain 3, one end of which is attached to the mounting assembly 2 and the opposite end of which is initially free so that it may be placed around the pipe P for engagement with the other side of the attachment assembly 2 in much the same fashion as a pair of oil field pipe tongs. A tightening mechanism is provided having a handle 4 by which the chain can be placed in tension so as to hold the end of the tester T firmly against the pipe P. Since this type of mechanism is known and forms no part of the present invention, it will not be further described hereafter.

Figure 2:
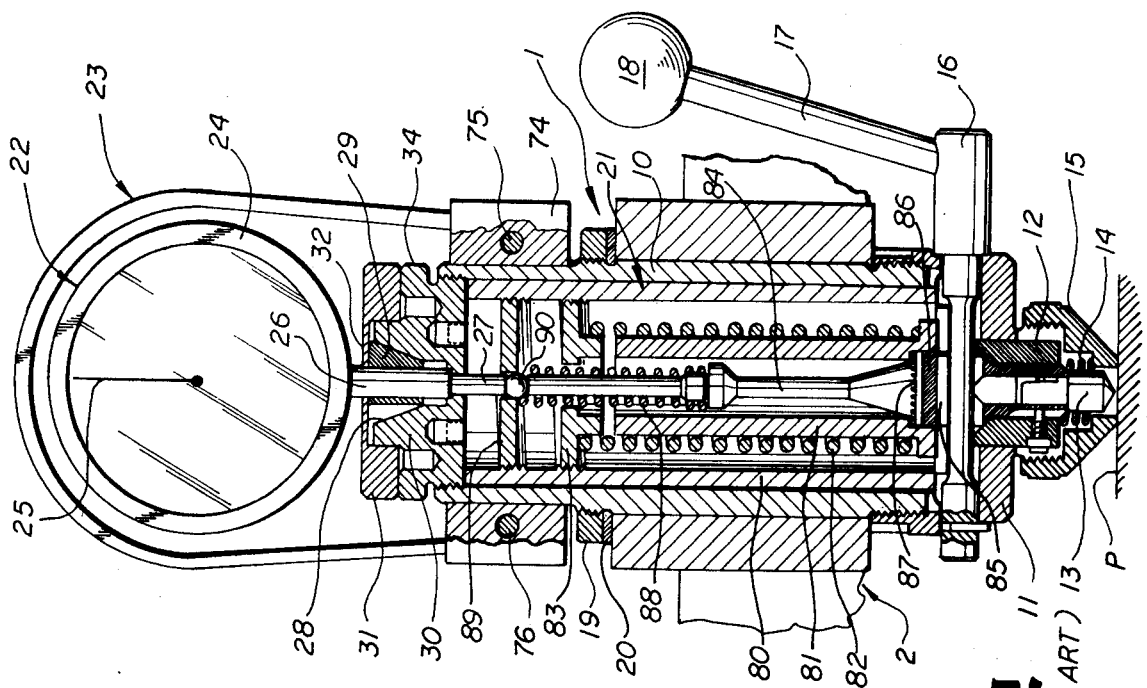
FIG. 2 is an elevation view, partially in section, of a tester illustrating prior art attachment of a dial gauge thereto.

Referring now to FIG. 2, the head unit 1 of the prior art tester T will be described in more detail. In this drawing, most of the mounting assembly 2 has been broken away so as not to interfere with the description of the tester head. The head unit 1 has a tubular housing 10 closed at the lower end by a threaded lower cap 11 through which is an aperture for receiving a seat member 12 and a reciprocating diamond penetrator 13. A spring 14 seats in the penetrator cap and creates a force against the seat 12. The spring 14 is held in place by a penetrator cap 15. The penetrator cap 15 rests against the pipe P or other material being tested. Extending through the lower cap is an operating cam 16 which engages the upper end of the seat member 13. An operating handle 17 and knob 18 are attached to the cam 16.

It will be noted that the tubular housing 10 of the tester T is received in the bore of the mounting assembly 2 and affixed thereto, the mounting assembly 2 being held between the shoulders of lower cap 11 and a lock nut and washer 19 and 20, respectively. Of course, various types of mounting assemblies can be utilized with such a tester unit.

The tester housing 10 receives a load cell 21, the lower end of which rests against the operating cam 16. Load cells 21 can be removed for repair or replacement by a different load cell.

Although load cells may be made in different ways, the one illustrated has a tubular housing 80 in which is centrally disposed a tubular spring mandrel 81, a major load spring 82 and a major load spring adjusting nut 83.

Centrally disposed in the bore of tubular spring mandrel 81 is a plunger rod 84 in the lower end of which the penetrator 13 is received. It will be noted that a horizontal hole 85 is provided in the lower enlarged portion 86 of the plunger rod 84. An upper shoulder of the enlarged portion 86 is provided with a thrust bearing 87 against which the major load spring mandrel rests and by which the force of major load spring 82 is transferred to the penetrator 13. Bearing against a shoulder on the upper end of plunger rod 84 is a minor load spring 88. The upper end of the minor load spring 88 bears against an adjustment nut 89. The upper end of plunger rod 84 terminates in a ball portion 90.

Attached at the upper end of the tester housing 10 is a dial gauge 22 and a dial gauge cover or protector 23. The cover or protector 23 can be attached to the tester housing 10 in any suitable fashion. In the embodiment shown, such attachment is provided by a split collar 74 and lock screws 75 and 76.

The dial gauge 22 includes a housing 24 in which is carried an operating mechanism (not shown). Also included is a dial indicator 25. At the base of the dial gauge 22 is a fixed stem 26 through which extends a reciprocating plunger 27. The plunger 27 is connected to the operating mechanism of the dial gauge 22 and movement of the plunger 27 effects movement of the dial indicator 25 in a conventional manner.

It will be noted that the end of the plunger 27 engages the well portion 90 of the plunger rod 84. To provide for such engagement, mounting apparatus is provided which includes a cap 34 threadedly attached to the tester housing 10. The cap 34 is provided with an aperture in which the stem 26 and plunger 27 are disposed for engagement of the plunger 27 with the plunger rod ball 90. The aperture flares upwardly and outwardly to form a frusto-conical surface 28 for receiving a frusto-conical collet 29. The upper portion of the lock cap 34 is threaded at 30 for engagement by corresponding internal threads of a lock nut 31. It will be noted that the lock nut 31 also has a central aperture and is counterbored so as to provide an end portion 32 which engages the upper surface of collet 29.

To mount the dial gauge 22, the dial cover 23 is removed and the lock nut 31 disengaged at least enough to allow the collet 29 to expand sufficiently to allow stem 26 to be inserted therethrough. The dial gauge 22 is held by the hand in the relative axial position desired and the lock nut 31 tightened so that the center 32 thereof is forced against the end of the collet 29 wedging it around the stem 26 due to the frusto-conical surface 28.

One can see that the amount of tightening force required is hard to determine with this sort of arrangement. If the collet 29 is not tightened sufficiently, the stem 26 may slip causing the readings of the tester to be in error. If tightened too much, the stem 26 may be damaged even to the extent of impairing the reciprocation of plunger 27. Furthermore, the axial disposition of the stem 26 and plunger 27 is hard to regulate with this sort of arrangement since tightening of the collet 29 is likely to move the stem 26 in a downward direction. Still further, if the dial gauge 22 must be removed for recalibration, repair or replacement, or if the load cell 21 must be changed, it is almost impossible to reinstall the dial gauge 22 in the same relative position with the tester housing 10 as before removal. Thus, such mounting of the prior art leaves much to be desired.

Although a complete description of the operation of the hardness tester shown in FIG. 2 is not necessary for understanding the mounting of dial gauge 22, it is helpful to know that movement of the cam 16 to various predetermined positions by handle 17 allows minor load, major load and no load to be applied against penetrator 13 by minor load spring 88 and major load spring 82. The indention of the material P being tested is followed by plunger rod 84. Consequently, the end of plunger 27 follows the ball portion 90 of the plunger tool 84 to measure the amount of penetration.

DESCRIPTION OF A PREFERRED EMBODIMENT

Figure 4:
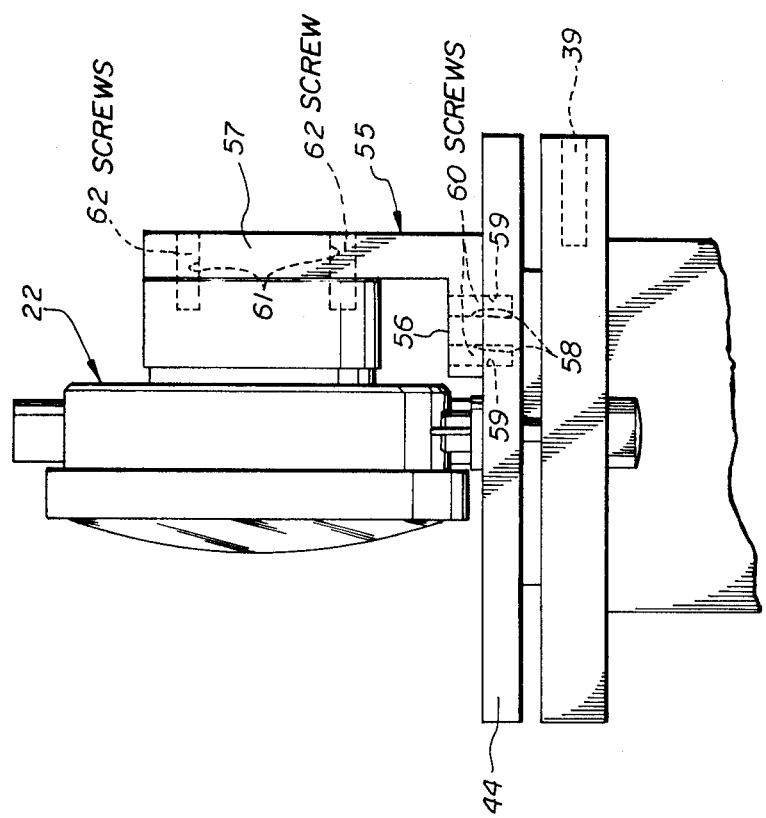
FIG. 4 is a side elevation view of the apparatus of FIG. 3, according to a preferred embodiment of the invention.
Figure 3:
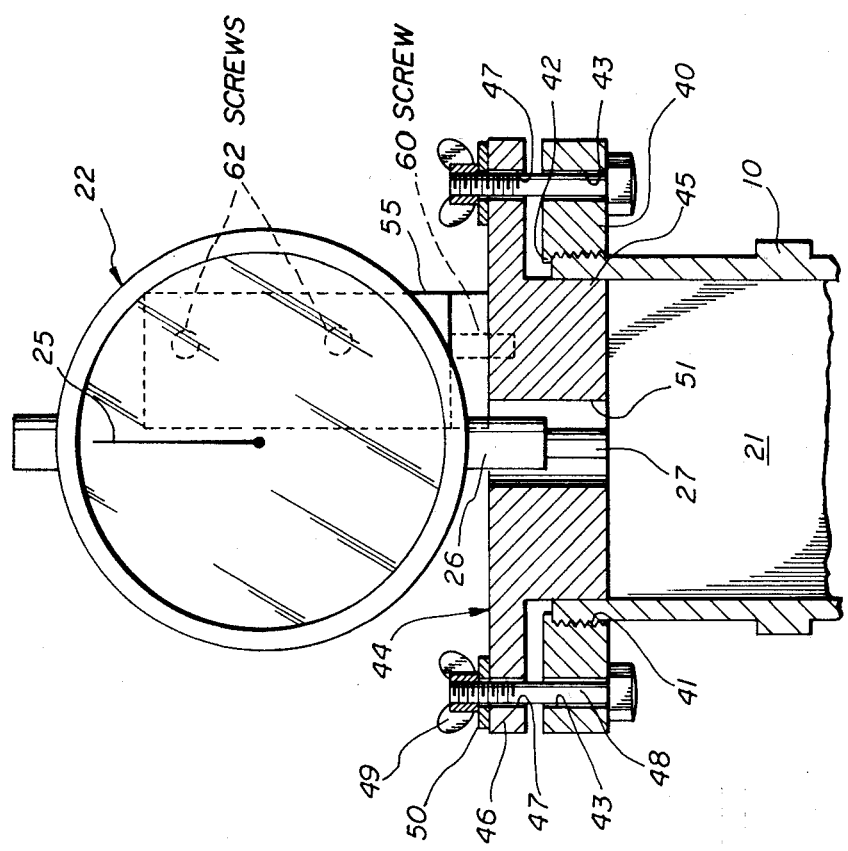
FIG. 3 is an elevation view, partially in section, of a dial gauge and associated mounting apparatus, according to a preferred embodiment of the invention, for attaching the dial gauge to a hardness tester.

Referring now to FIGS. 3 and 4, mounting apparatus for attaching a dial gauge to a hardness tester, according to a preferred embodiment of the invention, will be described. In these drawings, the tester housing 10, load cell 21 and the components of dial gauge 22, e.g. dial indicator 25, stem 26 and plunger 27, will be referred to by the same reference numbers.

In the preferred embodiment, a circular flange member 40 is attached to the upper end of the tester housing 10 by cooperating threads 41. At the upper end of the threaded aperture is provided an annular lip 42 which limits threaded engagement with the tester housing 10 and determines the axial position of the flange 40 relative to the tester housing 10. A radial set screw 39 (see FIG. 4) may be provided for engagement with the housing 10 to maintain this position. At least two holes 43 are provided on the periphery of the flange member 40.

Surmounted on the flange member 40 for closing the upper end of tester housing 10 is a circular cap member 44. The cap member 44 is provided with a cylindrical hub portion 45 which projects downwardly into the tester housing 10 for engagement with the upper end of load cell 21. The portion 46 of the cap member 44 which extends radially from the hub portion 45 is provided with holes 47 which correspond with the holes 43 in the flange member 40 so that threaded studs or bolts 48 may be received therein for engagement by wing nuts 49. A washer 50 may be placed beneath the wing nut 49. It will also be noted that a central aperture 51 is provided through the cap member 44.

Attached to the cap member 44 is a support member 55 which may be made from a piece of angle stock so as to be provided with a base portion 56 and an upwardly extending portion 57. The base portion 56 is provided with a pair of threaded holes 58 for registration with corresponding threaded holes 59 in the cap member 44 and in which screws 60 are threadedly engaged for attachment of the support member 55 to the cap member 44. The upper portion 57 of the support member 55 is provided with threaded holes 61 for receiving screws 62 which also threadedly engage corresponding holes in the back of dial gauge 22. Thus, the dial gauge is firmly affixed to the support member 55.

It will be noted that when the dial gauge 22 is firmly affixed to the support member 55, the stem 26 and plunger 27 are centrally and freely disposed in the aperture 51 of cap member 44. In fact, the dial gauge plunger 27 engages the load cell 21 in a predetermined relationship. In the testing operation, the plunger 27 responds to movement of the upper end of the plunger rod (not shown) centrally disposed with the load cell 21 for operation of the operating mechanism (not shown) of the dial gauge 22. This in turn causes the dial indicator 25 to move indicating the hardness of the material being tested.

If it is desired to remove the load cell 21 for replacement or repair, this can be easily done by simply removing the two wing nuts 49, allowing the cap member 44, support member 55 and dial gauge 22 to be removed from the tester housing 10 without relative movement therebetween. After the load cell 21 has been replaced, the cap member 44, support member 55 and dial gauge 22 can be reattached to the tester housing 10 by reengagement of the wing nuts 49 with the bolts or studs 48. When this is done, the support member 55 and the dial guage 22 are in the same relative position with the tester housing 10 as prior to the removal therefrom. Thus, no additional hand adjustment is required as in mounting apparatus of the prior art. Furthermore, since the dial gauge 22 is rigidly suspended from the support member 55, it is not necessary to grip the stem member 26 as in mounting systems of the prior art. Thus, the stem member 26 and plunger 27 are not subjected to damage as in prior art systems.

From the foregoing description, it can be seen that the mounting apparatus of the present invention for attaching a dial gauge to the housing of a hardness tester is far superior to systems of the prior art. It offers easy attachment and removal without potential damage to the gauge. In addition, the relationship of the plunger member to the load cell is predetermined, eliminating time-consuming adjustments. In addition to being simple to install and remove, the apparatus of the present invention is very economically manufactured. Use of the apparatus of the present invention will result in many hours of troublefree operation of the hardness tester with which it is used.

While a single embodiment of the invention has been described herein, many variations thereof can be made without departing from the spirit of the invention. Accordingly, it is intended that the scope of the invention be limited only by the claims which follow.

I claim:

1. Improved mounting apparatus for attaching a dial gauge to the housing of a hardness tester in which is carried a load cell, said dial gauge including a plunger extending from the base thereof for engagement with said load cell and responsive thereto for motivating the operating mechanism and indicator of said dial gauge, said mounting apparatus including a cap member attachable to the upper end of said housing and having a central aperture through which said dial gauge plunger projects for said engagement with said load cell wherein the improvement comprises:

a central hub portion provided on said cap member projecting downwardly into said housing for engagement with the upper end of said load cell, said dial gauge being attached to said cap member by a support member so that said dial gauge plunger is centrally and freely disposed in said aperture engaging said load cell in a predetermined axial relationship thereto; and a flange member attached to the upper end of said housing having at least two holes on the periphery thereof, corresponding holes in said cap member and threaded fastener members for engagement with said flange member holes and said corresponding cap member holes to hold said hub portion of said cap member against said load cell in a predetermined axial relationship.

2. Improved mounting apparatus as set forth in claim 1 in which said threaded fastener members are removable from said holes allowing said cap member and said dial gauge to be removed from said housing and subsequently reattached thereto in the same axial relationship with said load cell.

* * * * *